US00PP11853P2

(12) United States Plant Patent
Fleming et al.

(10) Patent No.: US PP11,853 P2
(45) Date of Patent: May 1, 2001

(54) HIBISCUS PLANT NAMED 'FANTASIA'

(75) Inventors: David W. Fleming; Gretchen A. Zwetzig, both of Lincoln, NE (US)

(73) Assignees: Fleming's Flower Fields, Inc.; David Fleming; Gretchen Zwetzig, all of Lincoln, NE (US)

( * ) Notice: Subject to any disclaimer, the term of this patent is extended or adjusted under 35 U.S.C. 154(b) by 0 days.

(21) Appl. No.: 09/289,838

(22) Filed: Apr. 12, 1999

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—Wendy A Baker

(57) ABSTRACT

A new and distinct cultivar of winter hardy hibiscus plant named 'Fantasia' is the result of a unique hybridization. This new and distinct cultivar is characterized primarily as to novelty by its extreme cold hardiness to Zone 4, its compact, rounded green "maple-cut" leaves, its medium-sized, ruffled lavender flowers with thick substance, its vigorous and compact growth habit, and its floriferous nature from mid-summer until frost.

3 Drawing Sheets

BACKGROUND OF THE NEW PLANT

The new plant of this invention is the result of a unique hybridization with the breeding achievement being evidenced in the outstanding combination of characteristics exhibited by this new and distinct hibiscus plant, which include:

(a) Refined and uniquely compact, green, 3-lobed leaves with a rounded and shortened lobe "maple-cut" which has relatively smooth margins and a numerous distribution throughout the plant that compliments landscape plantings;

(b) Exceptional lavender buds that open into medium-sized flowers that are outstanding for their lavender, thick textured petals with ruffling at the overlapping petal edges;

(c) The plant being floriferous with flowers that stay open at least one full day;

(d) The plant being small to medium sized, but vigorous, with extremely compact and uniform breaking action which gives it unique landscape utility; and, (e) The plant being so hardy that it can consistently withstand winter temperatures of at least −30 degrees Fahrenheit.

SUMMARY OF THE INVENTION

'Fantasia' was the result of a 40-year breeding program. It's ancestry includes various seedlings of *Hibiscus moscheutos* origin. More specifically, the seed parent of the instant plant is an un-named cultivar resulting from the cross of 'Dark Loveliness' (unpatented) (seed parent) and an unnamed *H. moscheutos* (pollen parent). The pollen parent of the instant plant is an unnamed *H. moscheutos*.

This new plant first bloomed in the summer of 1985 and was selected by David Fleming and Gretchen Zwetzig on the property in Lincoln, Nebr. owned by David Fleming. Asexual propagation of the plant by cuttings and root division in Lincoln, Nebr., has shown that the unique and distinguishing features of the plant are faithfully transmitted from generation to generation and appear to be firmly fixed.

Since its origin, the plant has bloomed from midsummer until frost, while exhibiting the above mentioned distinctive characteristics. This hardy hibiscus plant contributes to the market with its sheer beauty, its low-growing and very compact growth habit, its great resistance to disease and insects, its stability through extremes in rain and drought, and its extreme hardiness.

BRIEF DESCRIPTION OF THE DRAWINGS

The flower, bud, foliage and growth habit of the plant are shown in the attached illustrations.

More specifically, the first drawing shows the flower, bud, and some foliage in close view.

The second drawing is a close-up of the foliage.

The third drawing is a shot of the entire plant, just beginning to bloom. The colors illustrated are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE number designations are in accordance with the *Dictionary of Color* (Maerz and Paul), while general color recitations are consistent with ordinary American color terminology.

'Fantasia' has not been observed under all possible environmental conditions. It is to be understood that the phenotype may vary significantly with variations in environment such as temperature, light intensity, and day length, without, however any difference in genotype of the plant. The following botanical characteristics and observations are taken from a 5 year-old plant when grown under normal outdoor conditions in Lincoln, Nebr.

THE PLANT

Type of Plant: Hardy, Herbaceous perennial.
Classification: Hybrid Hibiscus plant.

Propagation: Relatively easy to propagate; fast rooting; holds its distinguishing characteristics through successive propagations by cuttings and division.

Size: Approximately 2 ft. 9 in. tall; about 2½ to 3 ft. wide.

Form: Symmetrical annual growth from perennial roots.

Habit: Upright and uniformly branched.

Growth: Vigorous; compact.

Hardiness: Hardy to at least −30° degrees Fahrenheit; heat tolerant to about 110 degrees Fahrenheit. General health: Plant is highly resistant to fungal diseases; highly resistant to pests such as Japanese beetle, white flies, aphids and spider mites; sturdy through excessive drought or water.

Foliage:

1. *Arrangement.*—Alternate.
2. *Shape.*—Juvenile — Palmate, refined, 3-lobed leaf; somewhat obtuse middle lobe. Mature — Very refined, palmate to hastate, 3-lobed leaf with somewhat serrulate margins and a more obtuse middle lobe; acute to acuminate apices; rounded to cordate base; compact.
3. *Size.*—Mature leaf — (petiole base to apex) length is about 4 inches (10.5 cm), width is about 3¼ inches (8.5 cm).
4. *Color.*—Young leaves (upper side) — L-3, page 69, PLATE 23. Mature leaves (upper side) — L-1, page 55, PLATE 16. Underside of leaves — H-4, page 69, PLATE 23.
5. *Surface texture.*—Glabrous with some luster.
6. *Petiole length.*—About 1½ inches (3 cm).
7. *Petiole color.*—Light green, close to L-1, p55 PL16 with a pink "blush" in the fall.

Stems: The stems are stout at the base, becoming more slender toward the apices; coloration is similar to the petiole.

THE FLOWER

Blooming Period: Profuse from midsummer until frost.

Flower diameter: Medium; about 8 inches (19.5 cm).

Borne: Singly in leaf axils, from midpoint of stems upward.

Bloom duration: Individual bloom lasts at least one full day. Typically, there are from 25 to 40 open blooms on the plant at at time in the landscape setting.

Form: Slightly ruffled and very overlapping. 5 petals per flora.

Bud:

1. *Length.*—About 3 inches (7.5 cm). Diameter: 1 to 1½ inches.
2. *Color.*—I-6, page 129, PLATE 53. Shape: Round to elongated.
3. *Duration.*—One week.

Corolla:

1. *Petal character and dimensions.*—Semi-ruffled where the petals overlap (greatly). Length is about 4 inches (10 cm). Width is about 5½ inches (14 cm).
2. *Coloration.*—Lavender with slight hints of grey and pink having an eyezone that is a reddish pink color about 2 inches in diameter). (a). Lavender petals-J-5, page 109, PLATE 43 ('Diadem'). (b) Eye zone — L-6, page 29, PLATE 3.
3. *Texture.*—Smooth.
4. *Substance.*—Thick.
5. *Shape.*—Ruffled and very overlapping; campanulate.

Reproductive organs:

1. *Staminal column.*—Stamen along basal two-thirds. Stamen length — About 2½ inches (6.5 cm). Stamen color — K-5, page 27, PLATE 2. Pollen color — K-4, page 41, PLATE 9.
2. *Style.*—Terminates upper one-third of Staminal column. Stigmatic lobe color — L-6, page 29, PLATE 3.

Calyx: Connate at the base; about 1¾ inches (4.5 cm) in length.

Stipules: None.

Epicalyx: Whorl of Bracts.

1. *Shape.*—8–12 slender, sword-shaped bractlets.
2. *Length.*—About 1 inch (2.5 cm).
3. *Color.*—L-6, page 67, PLATE 22.

Peduncles:

1. *Length.*—1½ inches (3.5 cm).
2. *Strength.*—Stiff and sturdy.

Fruit/seed: Seed set is minimal. Round seeds, about 1 cm in diameter, appear in rows inside of a rounded pod.

GENERAL OBSERVATIONS

This plant, as a hybridized hardy Hibiscus, is valuable to the landscape market for its compact stature, thicker textured and uniquely colored flowers that are a "color break" in the species, refined green "maple-cut" foliage, all-round vigor, full shrub-like habit, and adaptation to extreme environments, including the ability to survive winter temperatures of at least −30 degrees Fahrenheit.

We claim:

1. A new and distinct cultivar of hibiscus plant, as herein shown and described, characterized by its compact stature, its refined green "maple-cut" foliage, its ruffled Lavender flowers, its vigor, and its hardiness.

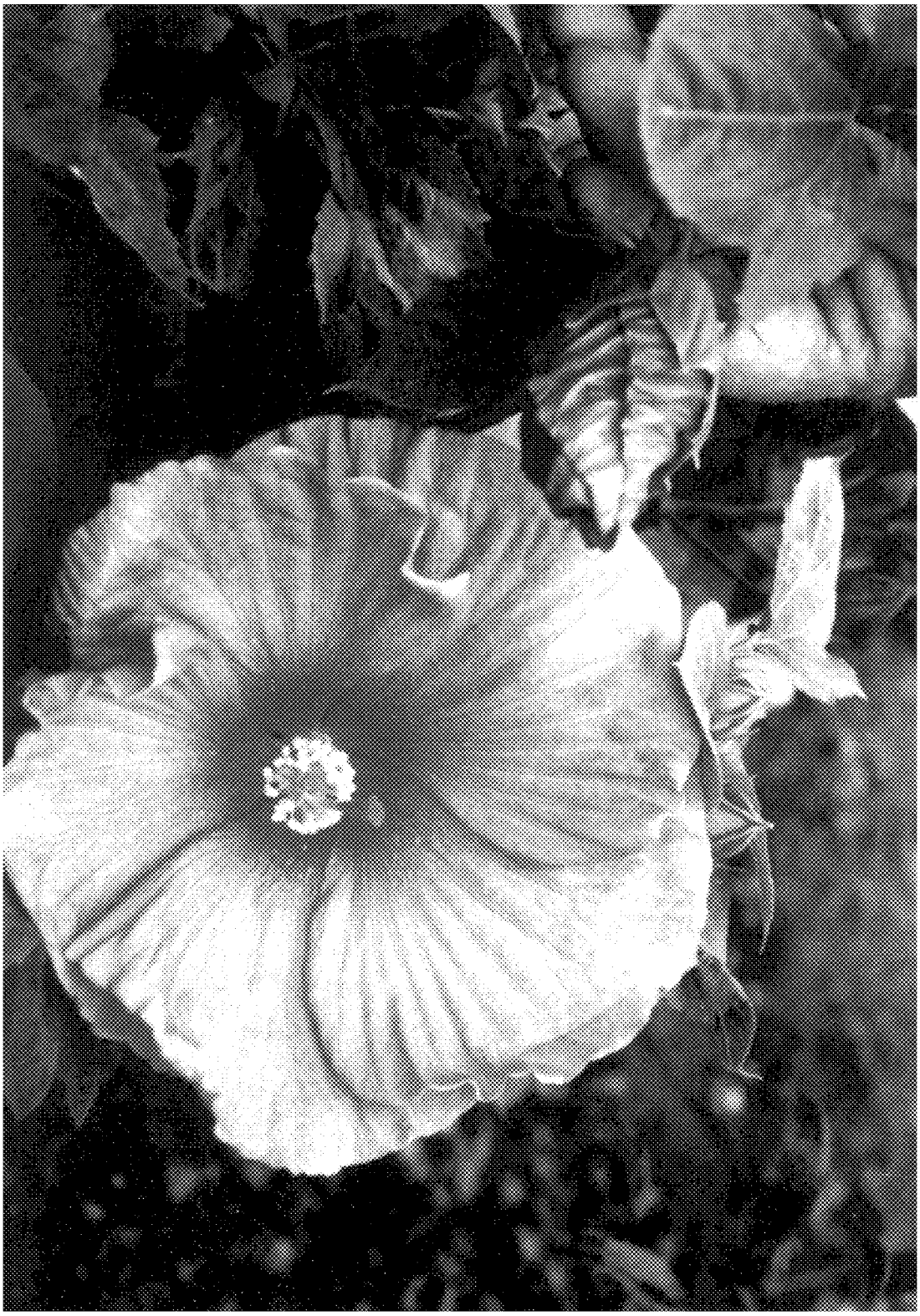

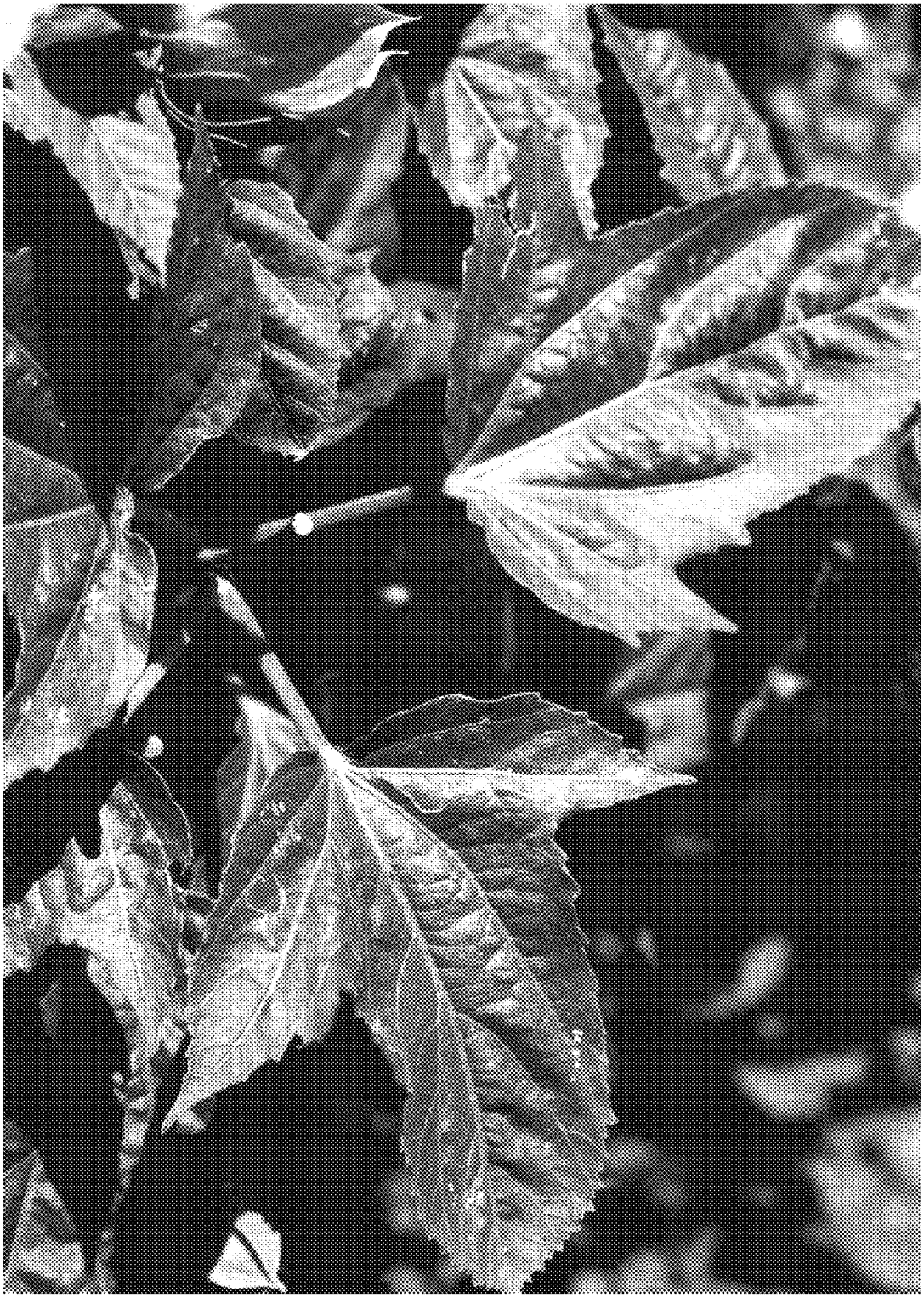

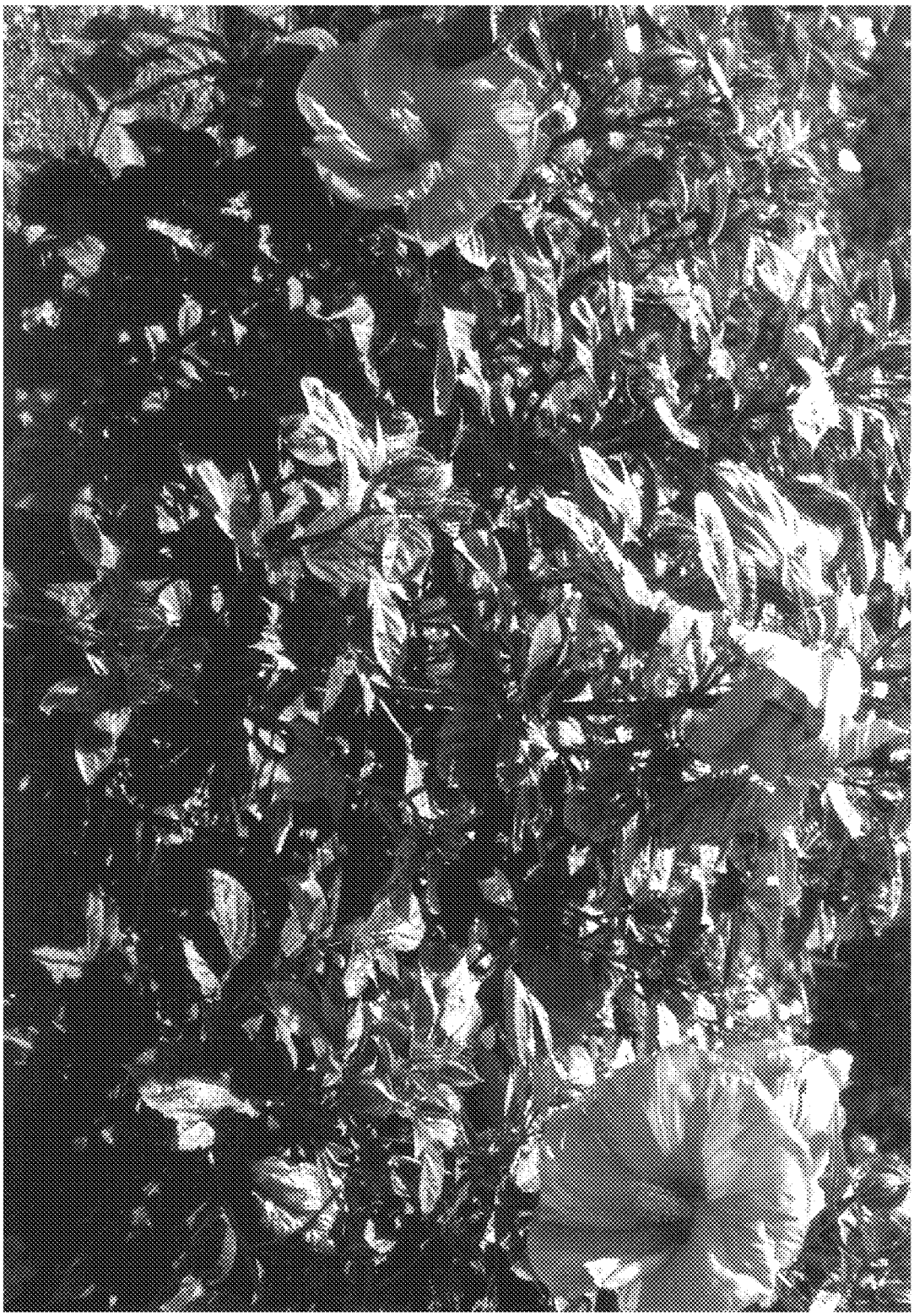

* * * * *